United States Patent [19]

Anderson

[11] Patent Number: 6,008,197

[45] Date of Patent: Dec. 28, 1999

[54] METHOD FOR INDUCING BONE FORMATION USING AN EXTRACT OF HUMAN OSTEOSARCOMA CELL LINE SAOS-2

[75] Inventor: H. Clarke Anderson, Shawnee Mission, Kans.

[73] Assignee: University of Kansas, Kansas City, Kans.

[21] Appl. No.: 07/683,283

[22] Filed: Apr. 10, 1991

Related U.S. Application Data

[63] Continuation-in-part of application No. 07/107,299, Oct. 9, 1987, Pat. No. 5,035,901.

[51] Int. Cl.[6] .......................... A61K 38/00; A61K 38/16; A61K 35/12; A23J 1/00
[52] U.S. Cl. ..................... 514/21; 514/2; 514/8; 424/573; 435/366; 530/417; 530/420; 530/828
[58] Field of Search ................ 435/240.2, 70.3, 435/366; 424/573; 530/828, 417, 420, 818; 514/2, 8, 21

[56] References Cited

U.S. PATENT DOCUMENTS

| | | | |
|---|---|---|---|
| 4,294,753 | 10/1981 | Urist | 260/112 |
| 4,394,370 | 7/1983 | Jeffries | 424/15 |
| 4,455,256 | 6/1984 | Urist | 260/112 R |
| 4,472,840 | 9/1984 | Jeffries | 3/1.9 |
| 4,526,909 | 7/1985 | Urist | 523/115 |
| 4,563,350 | 1/1986 | Nathan et al. | 424/95 |
| 4,563,489 | 1/1986 | Urist | 524/21 |
| 4,596,574 | 6/1986 | Urist | 623/16 |
| 4,619,989 | 10/1986 | Urist | 530/355 |
| 4,642,120 | 2/1987 | Nevo | 623/16 |
| 4,761,471 | 8/1988 | Urist | 530/350 |
| 4,968,590 | 11/1990 | Kuberasampath et al. | 530/326 |
| 5,035,901 | 7/1991 | Anderson et al. | 424/573 |

FOREIGN PATENT DOCUMENTS 169016 of 0000 European Pat. Off. .
212474 of 0000 European Pat. Off. .
WO8800205 of 0000 WIPO .

OTHER PUBLICATIONS

Amitani et al. (1975) Gann 66, 327–329.
Hanamura et al (1980) Clinical Ortho. Rel. Res. 148 281–290.
Takaoka et al. (1980) Clinical Ortho. Rel. Res. 148, 274–280.
Takaoka et al (1986) 1st International Workshop on Cells and Cytokines in Bone and Cartilage, S19. ab. 74.
Urist et al. (1979) Proced. Natl. Acad. Sci. 76, 1828–1832.
Takaoka et al. (1982) Clinical Ortho. Rel. Res. 164, 265–270.
Yoshikawa et al (1982) Clinical Ortho. Rel. Res. 163, 248–253.
Yoshikawa et al (1984) Clinical Ortho. Rel. Res. 182, 231–235.
Molecular Cloning: A Laboratory Manual, 2nd., ed., Sambrook et al, eds., Cold Spring Harbor Laboratory Press, Cold Spring Harbor, N.Y., 1989, p. 7.5.
Takaoka et al., Biomed. Res. 2(5): 466–471 (1981).
Anderson, Clin. Orthopaed. 119: 211–224 (1976).
Amitani et al., Clin. Orthopaed. & Rel. Res. 113: 164–167 (1975).
Amitani et al., Gann 66: 317–329 (1975).
Anderson et al., Am. J. Pathol. 44: 507–519 (1964).
Fogh et al, in Human Tumor Cells In Vitro, J. Fogh, ed. Plenum Press, N.Y. (1975) p. 120.

*Primary Examiner*—Deborah Crouck

[57] ABSTRACT

The invention relates to a method for inducing bone formation via administration of an extract of devitalized, freeze dried Saos-2 cells. The extract is prepared by contacting the freeze dried Saos-2 cells, which are devitalized in the act of freeze drying, with a weak denaturing agent of the type used to separate proteins from cells. It is not clear that the active ingredient in the extract is a protein; however, the extract does have properties superior to comparable treatment using whole Saos-2 cells. Also, described are the extracts themselves and various compositions containing it.

18 Claims, No Drawings

METHOD FOR INDUCING BONE FORMATION USING AN EXTRACT OF HUMAN OSTEOSARCOMA CELL LINE SAOS-2

RELATED APPLICATION

This application is a continuation-in-part of U.S. patent application Ser. No. 107,299, filed Oct. 9, 1987, now U.S. Pat. No. 5,035,901.

FIELD OF THE INVENTION

This invention relates to a method for inducing bone formation in a mammal. More specifically, it relates to such a method in which a bone forming effective amount of an extract of human osteosarcoma cell line Saos-2 is administered to the subject. Also disclosed is the extract used in the method, and a process for making it.

BACKGROUND AND PRIOR ART

The ability to induce bone formation and growth is an area of scientific inquiry which has seen a great deal of activity over the past 20–25 years. Initial observations by Urist et al, Science 150: 893–899 (1965), J. Dent. Res. 50: 1392–1406 (1971), that a substance residing in decalcified bone and now referred to as "bone morphogenic protein ("BMP" hereafter) could induce ectopic cartilage and bone formation via endochronal ossification after implantation adjacent to skeletal muscles and away from preexisting bone have led to research to isolate and to characterize this material, as well as to identify sources for it. Efforts have also been directed to identifying and isolating other materials having the same or similar properties. For example, a material herein referred to as "BIA" for bone inducing agent has been shown to exist in some strains of transformed, cultured human epithelial cells. Exemplary of this are Anderson et al. Am. J. Path. 44:507–519 (1964) and J. Cell Biol 33: 165–177 (FL transformed amnion cells). Anderson, et al, Fed. Proc. 27: 475 (1868) (HeLa cells). Wlodarski Exp. Cell Res. 57: 446–448 (1969) (WISH amnion cells); Wlodarski, et al Calcif. Tiss. Res. 7: 345–352 (1971); (neoplastic cells) Amitani et al., Gann 66: 327–329 (1975); Hanamura, et al., Clin. Orthop. & Rel. Res. 148: 274–280 (1980) (Dunn mouse osteosarcoma cells of BFO strain).

The patent literature in this field as it relates to BMP is growing. U.S. Pat. Nos. 4,294,753; 4,455,256; 4,526,909; 4,563,489; 4,596,574; 4,619,989; and 4,761,471, all issued to Urist, arise out of the work he has done on BMP. The most recent of these patents describes the isolation of BMP from frozen bone samples isolated from cadavers. Essentially, the bone was frozen, defatted, demineralized and freeze dried, after which a series of dissolving and dialyzing steps were carried out, ending in fractionation, dialysis, and SDS-PAGE analysis. The BMP is described as an acidic protein, with molecular weight of 17.5±0.5 kd for the human variety, whereas bovine BMP has molecular weight of 18.5±0.5 kd. The patent discusses how it is difficult to separate the bovine BMP from associated proteins, and how the associated proteins for both human and bovine BMP are necessary to optimize the effect of the protein on bone growth.

U.S. Patents have issued to others, as exemplified by U.S. Pat. Nos. 4,394,370; 4,472,840; 4,563,350; 4,642,120; and 4,968,590. For the most part, these patents deal with grafts for repairing osseous injuries. The '590 patent describes "pure mammalian osteogenic protein" and its uses. The protein, when glycosylated, has a molecular weight of 30 kd on SDS-PAGE, and is obtained from demineralized bone matrix. The bones are obtained from cattle. This protein may be identical to osteogenin, as described by Luyten et al, J. Biochem. 264: 13377–13380 (1989).

As the field has grown, it is convenient to refer to the class of proteins which have the specified effect as "BMPs". Thus, Wozney et al, Science 242: 1528–1534 (1989), have isolated genes for 3 BMPs, having molecular weights of 30, 18, and 16 kds. Recombinant BMPs have been produced via transfecting these genes into cultured monkey and hamster cells. Wang et al, Proc. Natl. Acad. Sci USA 87: 2220–2224 (1990), describe induction when BMP-2A is implanted in GuHCl inactivated, decalcified bone matrix carriers. Sampath et al, J. Biol. Chem. 265: 13198–13205 (1990), describe "osteoinductive protein" (OP), also isolated from demineralized bovine bone. The OP is a 30 kd dimer, having 16+18 kd subunits. This protein also induces bone when implanted with a GuHCl inactivated bone matrix carrier. Bentz et al, J. Biol. Chem 264: 20805–20810 (1989) have described "osteoinductive factor" (OIF) from bovine bone, and characterize it as a 22–28 kd protein which must react with TGF-beta to have osteoinductive effect in vivo. Bessho et al, Biochem. Biophys. Res. Comm. 165: 595–601 (1989), also isolated an osteoinductive protein of 18 kd.

Isolating protein from bone is an onerous task, requiring enormous amounts of raw materials for extremely small yields. The amount of processing involved cuts the available yield as well. Further, the source of the raw material (bone), must generally be animal. Given the diversity of individuals within an animal species, non-uniformity of protein from batch to batch is to be expected albeit being undesirable.

Given the drawbacks discussed supra, the use of cultured cells as a source of bone inducing agents and/or bone morphogenic proteins presents an attractive alternative. Cell masses can be grown up quickly, and when a cell line is used, one expects the protein to be uniform, since cell lines by definition are uniform.

The aforementioned cell lines, as indicated, are osteoinductive, but they are osteoinductive only when live cells are injected. The experiments showing this demonstrated efficacy using immunosuppressed animals. See Anderson, Connect. Tiss. Res. 24: 3–12 (1990); Anderson, et al., Am. J. Patho 44: 507–519 (1964); Wlodarski, et al., Calcif. Tiss. Res. 5: 70–79 (1970); Anderson et al, Fed. Proc. 27: 475 (1968). Implantation of live, foreign cells into a subject with a healthy or non-suppressed immune system will almost inevitably result in a strong, perhaps long term immunological response, so administration of live cells is not advisable. Also, when the cell line is tumorigenic, as most cell lines are, the ramifications of administering live cells include serious risks of transplating neoplasia into the subject. Monitoring the site of implantation with removal at a "critical point" is not possible, due to the risk of malignant invasion by the implant. The immediate suggestion, i.e., to introduce dead cells to the subject, has proven to be ineffective. Devitalized, freeze dried, FL, WISH, and HeLa cells, as well as their extracts, have not been effective as osteoinducing agents. Anderson et al, Clin. Orthop. Rel. Res. 119: 211–224 (1976).

It is rarely the case that one can obtain an osteoinductive cell line which has an effect when the cell line is devitalized. Workers out of the lab of Amitani and Takaoka, as per Amitani et al, Gann 66: 327–329 (1975); Takaoka, et al., Clin Orthop. Rel. Res. 164: 265–270 (1982); Takaoka, et al., Clin Orthop. Rel. Res. 144: 258–264 (1989), have reported positive results with an osteoinductive BFO strain of Dunn murine osteosarcoma, and human cell line H-OS-6. The aforementioned laboratory has not made these cell lines available to other researchers, so this work cannot be verified or compared to results with other cell lines. Also, as the art well knows, the odds of securing a second cell line with properties identical to a first one are astronomical. To be denied access to a cell line, even if one is aware of its lineage, renders it impossible for the artisan to repeat reported work. Even in the case where a researcher reports a detailed, careful protocol for how a cell line was produced, isolated or derived, repetition of this work hardly guarantees reproduction of the initial results. Hence, the existence of cell banks, depositories, and the general cordiality of researchers in sharing cell lines.

When treating humans, it is desirable to treat with material as close to native human material as possible. Against this back drop, applicant filed U.S. patent application Ser. No. 107,299 on Oct. 9, 1987 now issued as U.S. Pat. No, 5,035,901, evidencing the surprising ability of human osteosarcoma cell line Saos-2 to induce bone formation even in devitalized form. The results reported therein were surprising because (i) the prior publications in the field suggested that dead human cell lines were not osteoinductive, and (ii) comparison with many other cell lines showed that the properties of Saos-2 were not shared, either among other human cell lines or among other mammalian cell lines.

The work on Saos-2 has continued. It has now been found that extracts of Saos-2 not only possess osteoinductive effect but show properties superior to those possessed by the whole cells. This is surprising because the BIA from Saos-2 cell line is far from being characterized. Extraction protocols are known to damage some molecules, and in the process of extraction, one inevitably loses a portion of the starting material. With this lack of certainty in mind, it was thus more than slightly surprising that an Saos-2 extract, prepared as described infra, was effective in inducing bone formation in a subject. The investigations leading to this surprising result are described in the material which follows.

DETAILED DESCRIPTION OF PREFERRED EMBODIMENTS

EXAMPLE 1

Cell line Saos-2, described by Fogh et al, in Fogh, ed. *Human Tumor Cells In Vitro* (Plenum, N.Y. 115–159) (1975) were received as a gift; however, it may also be obtained from public sources, such as the American Type Culture Collection Under Accession Number ATCC HTB 85. This is a non-restricted culture.

The Saos-2 cells were seeded at a density of approximately $3 \times 10^4$ cells/cm$^2$ in either glass prescription bottles or in 150 cm$^2$ plastic "T" flasks. They were grown to confluence in approximately 1 week in Dulbecco's MEM, with 10% fetal calf serum, 2.2 mM L-glutamine added, penicillin (20 U/ml), amphotericin (50 ng/ml), and streptomycin (20 mg/ml) in 5% $CO_2$ atmosphere at 37° C. After reaching confluence, the cells were trypsinized, subdivided 1–4 or 1–5 and reseeded for further cell production. Approximately $2.0 \times 10^7$ confluent cells were released from one glass flask at time of trypsinization or scraping, and viability, studied by tryptan blue exclusion, was 95% or greater.

EXAMPLE 2

Confluent cultures of Saos-2 cells were gently rinsed twice with a sterile 0.9% sodium chloride solution to remove medium and stored at −70° C. until needed. For construction of the pellets of devitalized cells or BIA extracts, the cells were thawed, scraped with a rubber policemen and $8.0 \times 10^7$ cell aliquots were pelleted in 50 ml conical tubes by centrifugation at 2000 rpm for 10 minutes. The supernatant was discarded and the cells were defatted by resuspending the pellets in two washes of acetone. (Each wash was 5 times the volume of pellet). After acetone treatment, the cellular material was sedimented at 2000 rpm for 10 minutes and air dried at 4° C. for one hour. The resultant pellets were then freeze-dried, weighed and stored at −20° C. in a sterile, air tight container.

In order to facilitate retention of the pellets at the implantation site a collagen gel product (Vitrogen, Collagen Corporation, California) was mixed with the devitalized and defatted Saos-2 cell material. First, Saos-2 cells ($80 \times 10^6$ cells per implant) were dispersed in 300 µl of 0.01N HCl (40 µl acid per $10 \times 10^6$ cells) for 30 minutes at room temperature. Then, 700 µl of Vitrogen collagen gel, equal to the volume of the cell pellet and acid was added to the acidified pellet suspension. After further mixing, storage at room temperature for 3 hours and addition of 300 µl of 0.1M pH7 sodium phosphate buffer (the same volume as acid) the Saos-2 collagen pellets were stored at −20° C. In some experiments where pellets had been prepared with fewer than $80 \times 10^6$ cells, the quantity of collagen added was increased in order to maintain a relatively constant total volume of 1.4 to 1.6 ml per pellet. The Saos-2 collagen pellets were frozen, lyophilized and stored at −20° C. until implantation.

The pellets were used either "as is", or following extraction protocols. Examples 3 and 4, which follow, describe one extraction protocol using 4M guanidium hydrochloride (GuHCl), although similar results, not reported here, were also obtained using 6M urea, all other parameters being the same.

EXAMPLE 3

The defatted, freeze-dried Saos-2 cells were resuspended in 4M guanidium hydrochloride (Sigma), 0.1 g protein/10 ml of GuHCl (w/v) and continuously stirred at 4° C. for 48 hours. After extraction, the residual particulates were sedimented at 3000 RPM for 10 min. and discarded. The supernatant was placed in dialysis tubing with a 6000 to 8000 MW cut-off and dialyzed exhaustively against 0.05 M, pH 7.4 phosphate-buffered saline (PBS) at 4° C. for 24 to 48 hours. During dialysis, a precipitate formed that was pelleted and freeze-dried as described above. Before GuHCl extraction, each defatted and freeze-dried pellet derived from $100 \times 10^6$ Saos-2 cells weighed approximately 100 mg dry weight.

EXAMPLE 4

Small pellets ($0.7 \times 0.3$ cm) of freeze-dried defatted cells or of reprecipitated GuHCl extract of Saos-2 cells were implanted under metaphane anaesthesia beneath the latissimus dorsi muscles of Nu/Nu mice (obtained from Charles River Labs) and the skin incision was closed by stainless steel staples. At first, animals were sacrificed and implants were recovered after three weeks, but it was found with experience that only ten days to two weeks is required for full expression of cartilage, bone and bone marrow at the implantation site. Similar implants were prepared using the rat osteosarcoma cell line UMR-106, where the cells were also prepared as indicated supra.

EXAMPLE 5

At the time of sacrifice, the implants were removed, bisected, and one half of each implant was fixed for 24 to 48 hours in 10% phosphate-buffered formalin, embedded in paraffin and sectioned and stained by conventional histologic methods without a decalcification step. Although the implants showed extensive calcification after only 10 days, it was possible to make sections of the implants with reasonable facility without decalcification. In some instances the ossified implants were fixed in 2.5% glutaraldehyde in cacodylate buffer, post-fixed in osmium tetroxide, embedded in Spurr low-viscosity resin and sectioned at 1 micron thickness with toluidine blue stain for light microscopy or at 40 nM with lead citrate and uranyl acetate stains for electron microscopy. Electron microscopy was carried out using a Zeiss EM10-A electron microscope operating at 80 KV.

The unfixed halves of selected implants were homogenized in N-butanol, and the resultant butanol extract was analyzed for alkaline phosphatase specific activity following Hsu et al, Biochem. Biophys. Acta 913: 329–334 (1987) as a quantitative measure of ossification.

TABLE 1

| Type of Implant | no. with Bone/no. without Bone |
| --- | --- |
| defatted Saos-2 cells | 71/80 |
| reprecipitated GuHCl extract of Saos-2 cells | 31/32 |
| defatted UMR-106 cells | 0/6 |

EXAMPLE 6

The unique qualities of Saos-2 as an osteoinductive cell line were shown when comparative experiments were carried out, using various other osteosarcoma cell lines. Specifically, human osteosarcoma cell lines U2-OS, TE85 and MG63 were tested. The first two cell lines are available from the ATCC (HTB96, CRL 1543), while MG63 was a gift.

Following the same protocols for cell culture, preparation of pellets, and implants, the three cell lines listed above, plus UMR-106, and Saos-2 were tested in a side by side comparison. Six mice were tested using UMR-106 (8 pellets), 2 mice for MG63 (2 pellets), 3 mice for U2-OS (3 pellets), and thirteen mice (17 pellets) for Saos-2. Following cervical dislocation and analysis of the pellets when removed, all Saos-2 pellets showed bone, and some were very hard. The UMR-106 and TE-85 pellets remained soft, showing no bone cartilage or marrow formation. The site of UMR-106 pellet implantation showed inflammation as well. Similar negative results were obtained with MG63 and U2-OS.

The failure of any cell line other than Saos-2 to elicit bone formation led to the decision not to proceed with further extraction experiments on these cell lines.

EXAMPLE 7

An additional experiment was carried out to determine whether defatting, i.e., the use of acetone, was required for efficacy.

Either extraction with acetone or freeze drying will devitalize a cell, and in these experiments, cells were simply devitalized via freeze drying. Freeze drying, it will be recalled, only removes moisture from the cell sample.

Again, following the general protocols described supra, cells were grown up, pelleted, and implanted, the only difference being that in one set of experiments, no acetone extraction took place. These are the non-defatted cell lines.

In the following Table 2, the results for formation of bone, cartilage and marrow formation are presented summarizing the results of experiments on 3 animals. In this Table "+++" indicates much induction, "++" moderate induction, "+" a small amount, and "0" none whatsoever.

TABLE 2

| Animal No. | Bone | Cartilage | Marrow |
| --- | --- | --- | --- |
| DEFATTED | | | |
| 1 | ++ | ++ | ++ |
| 2 | ++ | ++ | + |
| 3 | ++ | ++ | + |
| NON-DEFATTED | | | |
| 1 | ++ | + | + |
| 2 | + | ' | 0 |
| 3 | + | + | + |

These results indicate that while acetone defatting improves the results, it is not an essential part of the procedure.

The foregoing examples demonstrate that bone induction was secured using an extract of devitalized Saos-2 cell lines. Data are presented for extracting the cell sample using 4M GuHCl, but as indicated supra, positive results were also obtained using 6M urea. Both solvents may be referred to as "weak denaturing agents," i.e., those materials which are known as permitting a protein to refold from whatever conformation possessed by the protein to one which is capable of exhibiting biological activity. This is the definition of a weak denaturing agent or solvent as set forth by, e.g., Builder et al, U.S. Pat. No. 4,511,502 which is incorporated by reference. Other solvents possessing this property are known to the skilled artisan and need not be repeated here.

Thus, the invention is a method for inducing bone formation in a mammal, such as a human by administering or treating the subject mammal in need of bone formation or healing with an amount of an extract of devitalized, freeze dried Saos-2 cells sufficient to promote bone healing or bone formation, wherein said extract is prepared by contacting freeze dried Saos-2 cells with a solvent containing a weak denaturing agent to form a supernatant and a sediment and separating the supernatant therefrom. The supernatant contains the bone inducing activity and may be further treated by, e.g., dialyzing against a salt solution with a low molecular weight cut-off point. A "low molecular weight cut-off" is e.g., 6000–8000 molecular weight. It will be understood that the specific dialysis step described herein, and other methods for concentrating the active material, available to the skilled artisan, including other dialysis protocols are optional. Following extraction, the extract is preferably treated to yield a precipitate. This precipitate may be pelleted and freeze dried, and administered to the subject mammal in that form.

Also described herein is the precipitate used in the treatment of the subject animal, prepared as described supra as are the freeze dried, devitalized Saos-2 cells per se. The extract, i.e., the precipitate, can be further treated to form a pellet, or can be combined with a pharmaceutically acceptable carrier to form a composition useful in inducing bone formation in a mammal.

As with the devitalized Saos-2 cells, the extract described herein can be used in the treatment of mammalian and veterinary diseases and neoplasms. An example of the latter is the use of the extract in the repair of large fractures or displacements, such as in equine and related species. Such fractures admit to treatment via splinting and/or bone replacement, using the extract described herein, either alone or in combination with biodegradable materials or pharmaceutical carriers. Similar efficacy is envisioned for, e.g., repair of deviated limbs in canine and other related species, as well as spine fusion.

The extract may be useful for systemic treatment to augment bone growth, to prevent bone loss in metabolic diseases such as osteoporosis, and to speed fracture healing and bone repair and bone replacement via systemic administration. In short, pathological conditions which result in general or specific bone loss, such as osteoporosis can be treated using the materials described herein. Other conditions which may be usefully treated include the replacement of bone removed for tumor surgery, for maxillofacial repair, to speed rigid fusion of vertebral bodies in spinal surgery ("slipped discs," scoliosis, etc), bone grafting, to speed healing of traumatic fractures, to augment bonding of resected bone surfaces to porous, biocompatible prostheses, to effect repair of non-uniform fractures, and so forth. Any of the conditions which the art speaks of being treatable by BMP or BMPs may be treated with the subject extract.

It will be understood that the specification and examples are illustrative but not limitative of the present invention and that other embodiments within the spirit and scope of the invention will suggest themselves to those skilled in the art.

What is claimed is:

1. Method for inducing bone formation in a mammal comprising administering an amount of an extract of Saos-2 cells sufficient to promote bone healing or bone formation to a mammal in need of said bone healing or bone formation, said extract of Saos-2 cells obtained by contacting a sample of devitalized, freeze dried Saos-2 cells with a denaturing agent in an amount and concentration to permit refolding of denatured protein to active form, or insufficient to denature protein to form a supernatant and a precipitate, wherein said supernatant is said extract.

2. Method of claim 1, wherein said denaturing agent is a solution of guanidium hydrochloride at a concentration insufficient to denature a protein.

3. Method of claim 1, wherein said denaturing agent is a solution of urea at a concentration which permits a protein to refold to a conformation which possesses biological activity.

4. Method of claim 2, wherein said guanidium hydrochloride is at a concentration of about 4M.

5. Method of claim 3, wherein said urea is at a concentration of about 6M.

6. Method of claim 1, wherein said extract of Saos-2 cells is obtained by treating a sample of devitalized, freeze dried Saos-2 cells with said denaturing agent to form a supernatant and a precipitate, removing said supernatant from said precipitate, and further treating said supernatant to form a second precipitate, wherein said second precipitate is said extract.

7. Method of claim 1, wherein said devitalized Saos-2 cells are defatted.

8. Method of claim 1, wherein said mammal is in need of healing of a bone defect treatment of a bone tumor or of promotion of assimilation of a bone graft.

9. Extract of Saos-2 cells useful in inducing bone formation, said extract prepared by contacting a sample of devitalized freeze dried Saos-2 cells with a solution of a denaturing agent in an amount and concentration to permit refolding of denatured protein to active form or insufficient to denature protein to form a supernatant and a precipitate, and separating said supernatant therefrom.

10. Extract of claim 9, wherein said denaturing agent is a solution of guanidium hydrochloride.

11. Extract of claim 9, wherein said denaturing agent is a solution of urea.

12. Extract of claim 10, wherein said solution of guanidium hydrochloride is at a concentration of about 4M.

13. Extract of claim 11, wherein said solution of urea is at a concentration of about 6M.

14. Extract of claim 9, in solution form.

15. Extract of claim 9, in pellet form.

16. Composition useful in inducing bone formation comprising the extract of claim 9 and a pharmaceutically acceptable carrier.

17. Composition of claim 16, wherein said pharmaceutical carrier is biodegradable.

18. Composition of claim 17, wherein said biodegradable pharmaceutical carrier is a matrix.

* * * * *